United States Patent
Lee et al.

(10) Patent No.: US 9,840,784 B2
(45) Date of Patent: Dec. 12, 2017

(54) ELECTROPLATING ADDITIVE AND PREPARATION METHOD FOR THE SAME

(71) Applicant: TAIWAN HOPAX CHEMS. MFG. CO., LTD., Kaohsiung (TW)

(72) Inventors: Kun-Hsin Lee, Kaohsiung (TW);
Ying-Jin Chen, Kaohsiung (TW);
Tzu-Hua Feng, Kaohsiung (TW);
Li-Jane Her, Kaohsiung (TW);
Chia-Jun Chiang, Kaohsiung (TW)

(73) Assignee: TAIWAN HOPAX CHEMS. MFG. CO., LTD., Kaohsiung (TW)

( * ) Notice: Subject to any disclaimer, the term of this patent is extended or adjusted under 35 U.S.C. 154(b) by 0 days.

(21) Appl. No.: 15/202,620

(22) Filed: Jul. 6, 2016

(65) Prior Publication Data

US 2017/0029970 A1 Feb. 2, 2017

(30) Foreign Application Priority Data

Jul. 28, 2015 (TW) .............................. 104124347 A (51) Int. Cl.
| | |
|---|---|
| *C25D 3/12* | (2006.01) |
| *C07C 323/66* | (2006.01) |
| *C25D 3/32* | (2006.01) |
| *C25D 3/38* | (2006.01) |
| *C07C 323/52* | (2006.01) |
| *C25D 3/30* | (2006.01) |

(52) U.S. Cl.
CPC .............. *C25D 3/12* (2013.01); *C07C 323/52* (2013.01); *C07C 323/66* (2013.01); *C25D 3/30* (2013.01); *C25D 3/32* (2013.01); *C25D 3/38* (2013.01)

(58) Field of Classification Search
CPC ....... C07C 1/00; C07C 323/52; C07C 323/66; C25D 3/12; C25D 3/30; C25D 3/32; C25D 3/38
See application file for complete search history.

(56) References Cited

U.S. PATENT DOCUMENTS 6,946,024 B2 * 9/2005 Soga ..................... C09D 11/38
106/31.27

FOREIGN PATENT DOCUMENTS

| JP | 49-5196 A | * | 1/1974 |
| JP | 07-70052 A | * | 3/1995 |
| JP | 10-306396 A | * | 11/1998 |

* cited by examiner

*Primary Examiner* — Anthony J Green
(74) *Attorney, Agent, or Firm* — Bacon & Thomas, PLLC (57) ABSTRACT

The present invention provides a carboxyl sulfonate compound and preparation method thereof. The present carboxyl sulfonate compound has structure of formula (A):

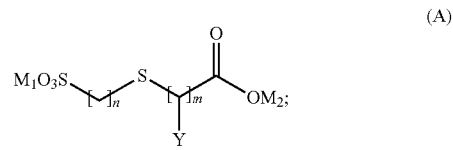

(A)

wherein $M_1$ is hydrogen or an alkali metal; $M_2$ is hydrogen, alkyl or an alkali metal; Y is hydrogen, alkyl; carboxyl, carboxyl salt; alkylcarboxyl, or alkylcarboxyl salt; n is an integer from 1 to 10; and m is an integer from 1 to 10. The carboxylic group and the sulfonic acid group in the structure of the present carboxyl sulfonate compound show excellent chelating ability to metal ions; therefore, the present carboxyl sulfonate compound is particularly for use in electroplating additive.

15 Claims, 6 Drawing Sheets

ELECTROPLATING ADDITIVE AND PREPARATION METHOD FOR THE SAME

BACKGROUND

Technical Field

The present invention is related to an electroplating additive, especially to an additive for electroplating processes such as lead-free plating, copper plating, tin plating, nickel plating, etc.

Description of Related Art

Electroplating is a common manufacturing process in modern industry. In the wake of the improvement of industrial technology and the raising demand of the consumer to the fineness of the product appearance, it is very common in the field to add some certain metal salts, metal oxides, aromatic compounds, and/or heterocyclic compounds (so called electroplating additives) to obtain smoother and brighter electroplated metal layer.

Sulfosuccinin acid sodium salt (SSSA) and sodium 3-mercapto-1-propanesulfonate (MPS) are two of the conventional electroplating additives in the fields. However, it tends to produce sulfur dioxide gas when sulfosuccinin acid sodium salt is being produced, which increases risks to the working environment and concerns of pollution. Sodium 3-mercapto-1-propanesulfonate is also not an ideal additive because it includes unstable thiol bonds in structure and its property tends to be altered in the case of repeated uses.

Accordingly, in order to satisfy the demand of fineness of electroplating process in nowadays industry, it needs more options of electroplating additives.

SUMMARY

In light of the foregoing, one of the objectives of the present invention is to provide a novel compound and preparation method thereof. The preparation of the compound is simple and would not produce noxious gas. The compound can be added to the electroplating solution to improve the quality of electroplating.

Another objective of the present invention is to provide an electroplating additive, which has stable property and would not tend to be altered even in repeated uses.

In order to achieve the aforesaid objectives, the present invention provides a carboxyl sulfonate compound of formula (A):

(A)

wherein, $M_1$ is hydrogen or an alkali metal; $M_2$ is hydrogen, alkyl, or an alkali metal; each Y is independently hydrogen, alkyl, carboxyl, carboxyl salt, alkylcarboxyl, alkylcarboxyl salt or ester; n is an integer from 1 to 10; and m is an integer from 1 to 10.

Preferably, at least one of Y is carboxyl, carboxyl salt, alkylcarboxyl, alkylcarboxyl salt or ester.

Preferably, each Y is independently of formula (B):

(B)

wherein $M_3$ is hydrogen, alkyl, or alkali metal; and
wherein the * is where the formula (B) connects to the formula (A).

Preferably, said alkali metal is lithium, sodium, or potassium.

Preferably, said alkyl is $C_1$-$C_3$ alkyl.

Preferably, at least one of $M_2$ and $M_3$ is an alkali metal.

Preferably, $M_1$ is an alkali metal, $M_2$ and $M_3$ are both hydrogen, n is 3, and m is 1.

Preferably, $M_1$ is an alkali metal, $M_2$ and $M_3$ are both alkyl, n is 3, and m is 1.

Preferably, $M_1$ is an alkali metal, one of $M_2$ and $M_3$ is alkyl and the other one is an alkali metal, n is 3, and m is 1.

Preferably, said carboxyl sulfonate compound is of formula (C):

(C)

wherein, $M_1$ is hydrogen or an alkali metal; $M_2$ is hydrogen, alkyl, or an alkali metal; $Y_1$ and $Y_2$ are independently hydrogen, alkyl, carboxyl, carboxyl salt, alkylcarboxyl, or alkylcarboxyl salt; and n is an integer from 1 to 10.

Preferably, $M_1$ is an alkali metal, $M_2$ is hydrogen, n is 3, $Y_1$ is hydrogen, $Y_2$ is hydrogen or alkyl.

Preferably, said carboxyl sulfonate compound is used as a glazing agent for electroplating.

The present invention also provides an electroplating additive, comprising: the aforesaid carboxyl sulfonate compound; and a solvent; wherein a weight percent of said carboxyl sulfonate compound is contained 0.01 to 50 weight percent of said electroplating additive based on a total weight thereof at a temperature of 27±3° C.

Preferably, said solvent is water.

Preferably, said electroplating is lead-free plating, copper plating, tin plating, nickel plating, or a combination thereof.

The present invention further provides a preparation method for a carboxyl sulfonate compound; wherein said carboxyl sulfonate compound is of formula (A):

(A)

wherein, $M_1$ is hydrogen or an alkali metal; $M_2$ is hydrogen, alkyl, or an alkali metal; Y is independently hydrogen, alkyl, carboxyl, carboxyl salt, alkylcarboxyl, or alkylcarboxyl salt; n is an integer from 1 to 10; and m is an integer from 1 to 10;

wherein said method comprises reacting a compound of formula (D) with a compound of formula (E); wherein said compound of formula (D) comprises the following structure:

wherein, $M_1$ is hydrogen and n is an integer from 1 to 10; and said compound of formula (E) comprises the following structure:

wherein $R_1$ is hydrogen or alkyl; and $R_2$ is hydrogen, alkyl, alkenyl, alkylalkenyl, alkenylcarboxyl, alkenylester; or $R_2$ is an alkylcarboxyl and said carboxyl thereof forms a ring with said R1.

Preferably, said compound of formula (E) is maleic anhydride, maleic acid, dialkyl maleate, acrylic acid, or methacrylic acid.

Preferably, said compound of formula (A) is said carboxyl sulfonate compound as set forth in the preceding paragraphs.

Preferably, provided that $M_2$ of said the compound of formula (A) is alkali metal, said method further comprises reacting the product obtained from the reaction between said compound of formula (D) and said compound of formula (E) with an alkali metal hydroxide.

Preferably, the reaction between said compound of formula (D) and said compound of formula (E) is conducted at a temperature of 20 to 60° C.

Preferably, said method further comprises a purification step: applying the product obtained from the reaction between said compound of formula (D) and said compound of formula (E) through an anion exchange resin to obtain an elute; wherein said elute contains said compound of formula (A). Preferably, said anion exchange resin comprises strongly basic anion exchange resin, weakly basic anion exchange resin, or a combination thereof.

Preferably, said method further comprises a crystallization step: crystallizing said elute in an alcohol solution to obtain a solid form of said compound of formula (A).

To sum up, the present invention provides a novel compound and a preparation method for said compound thereof. The compound of present invention could be used as an electroplating additive and has the advantages of stable property and safe preparing method so that provides an alternative for the electroplating demand in the field.

DETAILED DESCRIPTION

The present invention is related a novel compound which could be used as an electroplating additive. Said compound comprises two carboxyl groups and one sulfonic acid group and thereby is able to exhibit excellent chelating ability to metal ions. The preparation of said compound would not produce noxious gas so that has lower safety concern in operation and less adverse effects on environment. Moreover, the present compound has stable structure so that the property of the present compound would not tend to be altered in repeated uses.

In the first aspect of the present invention, the present compound is of formula (A):

wherein, $M_1$ is hydrogen or an alkali metal; $M_2$ is hydrogen, alkyl, or an alkali metal; Y is independently hydrogen, alkyl, carboxyl, carboxyl salt, alkylcarboxyl, or alkylcarboxyl salt; n is an integer from 1 to 10; and m is an integer from 1 to 10.

In an alternative embodiment, Y is of formula (B):

wherein $M_3$ is hydrogen, alkyl, or alkali metal.

In the second aspect of the present invention, the present compound is of formula (C):

$M_1$ is hydrogen or an alkali metal; $M_2$ is hydrogen, alkyl, or an alkali metal; $Y_1$ and $Y_2$ are independently hydrogen, alkyl, carboxyl, carboxyl salt, alkylcarboxyl, or alkylcarboxyl salt; and n is an integer from 1 to 10.

In an alternative embodiment, the present compound is of formula (1):

(1)

wherein $M_1$, $M_2$, $M_3$ is independently hydrogen, alkyl, or alkali metal, n is an integer from 1 to 10. In a preferably embodiment, $M_1$, $M_2$, $M_3$ are all hydrogen. In an alternative embodiment, said alkali metal is lithium, sodium, or potassium.

In an alternative embodiment, some examples of the compound of formula (1) are listed in the following Table 1.

TABLE 1

| Example | $M_1$ | $M_2$ | $M_3$ | n |
|---|---|---|---|---|
| 1 | Na | H | H | 3 |
| 2 | Na | H | Na | 3 |
| 3 | Na | Na | H | 3 |
| 4 | Na | Na | Na | 3 |
| 5 | Na | $CH_3$ | $CH_3$ | 3 |
| 6 | Na | $CH_3$ | H | 3 |
| 7 | Na | $CH_3$ | Na | 3 |
| 8 | Na | H | $CH_3$ | 3 |
| 9 | Na | Na | $CH_3$ | 3 |
| 10 | Na | $CH_2CH_3$ | $CH_2CH_3$ | 3 |
| 11 | Na | $CH_2CH_3$ | $CH_3$ | 3 |
| 12 | Na | $CH_2CH_3$ | H | 3 |
| 13 | Na | $CH_2CH_3$ | Na | 3 |
| 14 | Na | $CH_3$ | $CH_2CH_3$ | 3 |
| 15 | Na | H | $CH_2CH_3$ | 3 |
| 16 | Na | Na | $CH_2CH_3$ | 3 |
| 17 | K | H | H | 3 |
| 18 | K | H | K | 3 |
| 19 | K | K | H | 3 |
| 20 | K | K | K | 3 |
| 21 | K | $CH_3$ | $CH_3$ | 3 |
| 22 | K | $CH_3$ | H | 3 |
| 23 | K | $CH_3$ | K | 3 |
| 24 | K | H | $CH_3$ | 3 |
| 25 | K | K | $CH_3$ | 3 |
| 26 | K | $CH_2CH_3$ | $CH_2CH_3$ | 3 |
| 27 | K | $CH_2CH_3$ | $CH_3$ | 3 |
| 28 | K | $CH_2CH_3$ | H | 3 |
| 29 | K | $CH_2CH_3$ | K | 3 |
| 30 | K | $CH_3$ | $CH_2CH_3$ | 3 |
| 31 | K | H | $CH_2CH_3$ | 3 |
| 32 | K | K | $CH_2CH_3$ | 3 |

In an alternative embodiment, the present invention compound is of formula (2):

(2)

wherein, $M_1$ is hydrogen or an alkali metal; $M_2$ is hydrogen, alkyl, or an alkali metal; $Y_2$ is hydrogen or alkyl; and n is an integer from 1 to 10. In an alternative embodiment, said alkali metal is lithium, sodium, or potassium.

In an alternative embodiment, some examples of the compound of formula (2) are listed in the following Table 2.

TABLE 2

| Example | $M_1$ | $M_2$ | $Y_2$ | n |
|---|---|---|---|---|
| 33 | Na | H | H | 3 |
| 34 | Na | H | $CH_3$ | 3 |
| 35 | Na | H | $CH_2CH_3$ | 3 |
| 36 | Na | Na | H | 3 |
| 37 | Na | Na | $CH_3$ | 3 |
| 38 | Na | Na | $CH_2CH_3$ | 3 |
| 39 | K | H | H | 3 |
| 40 | K | H | $CH_3$ | 3 |
| 41 | K | H | $CH_2CH_3$ | 3 |
| 42 | K | K | H | 3 |
| 43 | K | K | $CH_3$ | 3 |
| 44 | K | K | $CH_2CH_3$ | 3 |

The third aspect of the present invention provides an electroplating additive, comprising the carboxyl sulfonate compound of the present invention and a solvent. In an alternative embodiment, the weight percent of said carboxyl sulfonate compound in said electroplating additive is 0.01 to 50 weight percent based on a total weight thereof at a temperature of 27±3° C. In an alternative embodiment, said solvent is water.

In an alternative embodiment, the present compound can be formulated as said electroplating additive of the present invention and then be used for electroplating process; or the present compound can be added with other necessary components into the electroplating solution required for the electroplating process. Said other components are the components necessary for an electroplating solution, including but not limited to: main salt (depending the kind of the electroplating), auxiliary agent, diffusing agent, or a combination thereof. In a preferable embodiment, the electroplating solution formulated with the present compound or the present electroplating additives would not need to add any fluoro-containing compound.

In the fourth aspect of the present invention, the present invention provides a preparation method for a carboxyl sulfonate compound; wherein said carboxyl sulfonate compound is of formula (A):

(A)

wherein, $M_1$ is hydrogen or an alkali metal; $M_2$ is hydrogen, alkyl, or an alkali metal; Y is independently hydrogen, alkyl, carboxyl, carboxyl salt, alkylcarboxyl, or alkylcarboxyl salt; n is an integer from 1 to 10; and m is an integer from 1 to 10;

wherein said method comprises reacting a compound of formula (D) with a compound of formula (E); wherein said compound of formula (D) is of the following structure:

(D)

wherein, $M_1$ is hydrogen and n is an integer from 1 to 10; and wherein said compound of formula (E) is of the following structure:

(E)

wherein $R_1$ is hydrogen or alkyl; and $R_2$ is hydrogen, alkyl, alkenyl, alkylalkenyl, alkenylcarboxyl, alkenylester; or $R_2$ is an alkylcarboxyl and said carboxyl thereof forms a ring with said $R_1$.

In an alternative embodiment, said compound of formula (D) is sodium 3-mercapto-1-propanesulfonate having the following structure:

In an alternative embodiment, said compound of formula (E) is maleic anhydride, maleic acid, dialkyl maleate, acrylic acid, or methacrylic acid. In a preferable embodiment, said compound of formula (E) is maleic anhydride having the following structure:

In an alternative embodiment, provided that $M_2$ of the compound of formula (A) is alkali metal, said method further comprises reacting the product obtained from the reaction between said compound of formula (D) and said compound of formula (E) with an alkali metal hydroxide.

In an alternative embodiment, provided that the compound of formula (A) is of formula (1) and at least one of $M_2$ and $M_3$ is alkali metal, said method further comprises reacting the product obtained from the reaction between said compound of formula (D) and said compound of formula (E) with an alkali metal hydroxide.

In an alternative embodiment, said method further comprises a purification step: applying the product obtained from the reaction between said compound of formula (D) and said compound of formula (E) through an anion exchange resin to obtain an elute; wherein said elute contains said compound of formula (A). Said anion exchange resin comprises strongly basic anion exchange resin, weakly basic anion exchange resin, or a combination thereof.

In an alternative embodiment, said method further comprises a crystallization step: crystallizing said elute in an alcohol solution to obtain a solid form of said compound of formula (A). Alternatively, said crystallization step is conducted by placing said elute steadily at a temperature of 0 to 60° C.

The following specific examples are going to describe a specific preparation example of the present compound and its specific formulation into electroplating solutions for electroplating. The contents of the following examples are exemplary and shall not be used for limiting the claim scope of the present invention. Those having ordinary skill in the art are able to make modification and alteration based on the disclosure of the instant specification and the general knowledge in the field but still be within the scope of the present invention.

Experiment 1: Preparation of the Compound of the Present Invention

A specific example of the compound of formula (1) of the present invention was prepared in this experiment. First of all, 3-mercapto-1-propanesulfonate (294.05 g) was put into a reactor and then water (600 g) was introduced to dissolve it fully. Afterward, the temperature of the reactor was raised to 50° C. and maleic anhydride (147.09 g) was added in various batches under stirring. After that, the temperature of the reactor was maintained at between 50 to 60° C. and the contents inside were kept stirring for one hour to obtain a reaction mixture. Then, the reaction mixture was passed through an anion exchange resin column (Mitsubishi, DIAION UBA120P) and filtered through a 0.22 μm filter to obtain an elute. Afterward, the elute was concentrated by filtration under reduced pressure and crystallized by methanol to obtain crystals. Then, the crystals were heated at 60° C. for one hour. After filtration by suction and drying, 190 g of product was obtained and the yield rate of this experiment is 64.6%.

Figure 1:
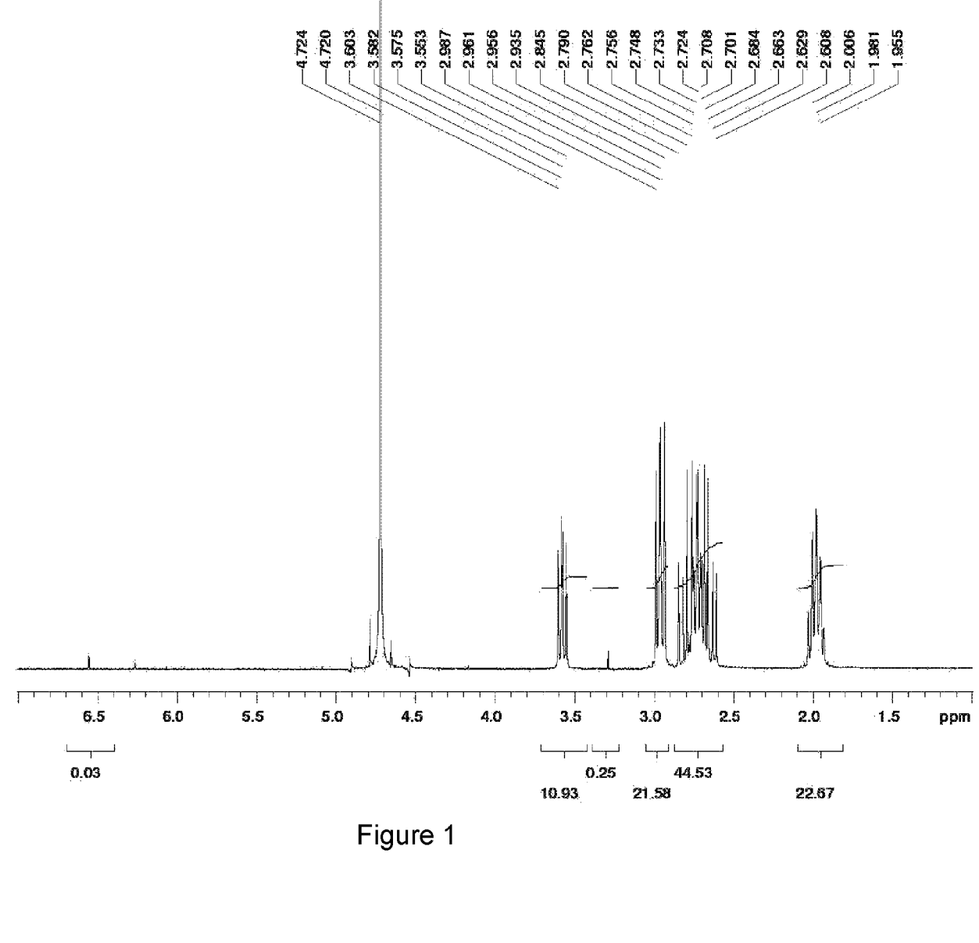
FIG. 1 displays the NMR $H^1$ spectrum of the compound synthesized in Experiment 1 of the present invention.
Figure 2:
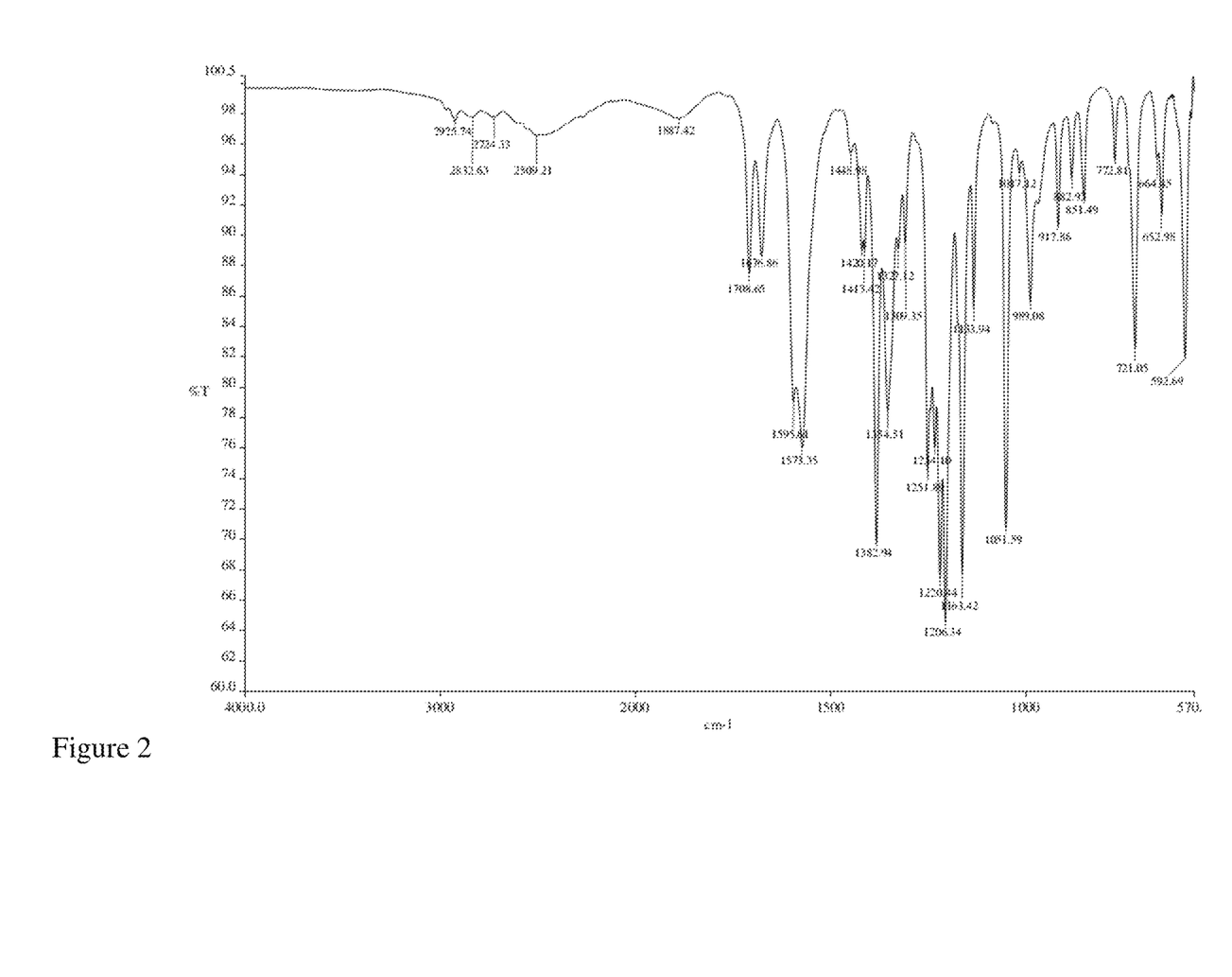
FIG. 2 shows the IR spectrum of the compound synthesized in Experiment 1 of the present invention.

The product of the aforesaid experiments was analyzed by NMR H1 spectrum and IR spectrum ($D_2O$ was used as solvent, conducted at room temperature). The results were shown in FIG. 1 and FIG. 2. According to the spectrum analysis, the compound synthesized in this experiment has the following structure:

(Sample 1)

Lastly, the Sample 1 compound was dissolved in water and formulated as electroplating additive of 10, 20, and 50 weight % respectively.

Experiment 2: Preparation of the Compound of the Present Invention

A specific example of the compound of formula (1) of the present invention was prepared in this experiment. First of all, 3-mercapto-1-propanesulfonate (169.3 g) was put into a reactor and then water (475 g) was introduced to dissolve it fully. Afterward, the temperature of the reactor was raised to 50° C. and maleic anhydride (147.09 g) was added in various batches under stirring. After that, the temperature of the reactor was maintained at between 50 to 60° C. and the contents inside were kept stirring for one hour to obtain a reaction mixture. Then, NaOH (45 wt %) was added while the reaction mixture was placed in ice bath until the pH value of the reaction mixture reached 6.4. Afterward, the reaction mixture was passed through an anion exchange resin column (Mitsubishi, DIAION UBA120P) and filtered through a 0.22 μm filter to obtain an elute. Afterward, the elute was concentrated by filtration under reduced pressure and crystallized by methanol to obtain crystals. Then, the crystals were heated at 60° C. for one hour. After filtration by suction and drying, 220 g of product was obtained and the yield rate of this experiment is 65.1%.

Figure 3:
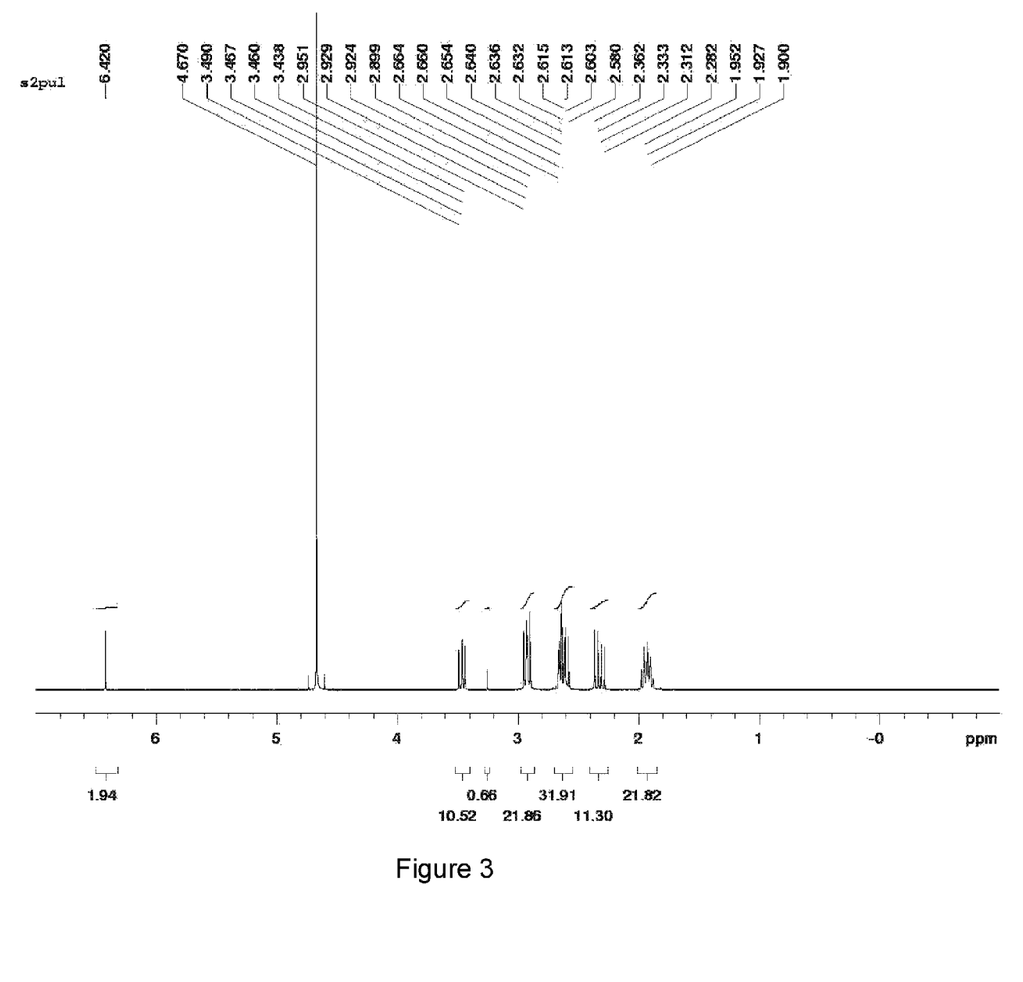
FIG. 3 displays the NMR $H^1$ spectrum of the compound synthesized in Experiment 2 of the present invention.
Figure 4:
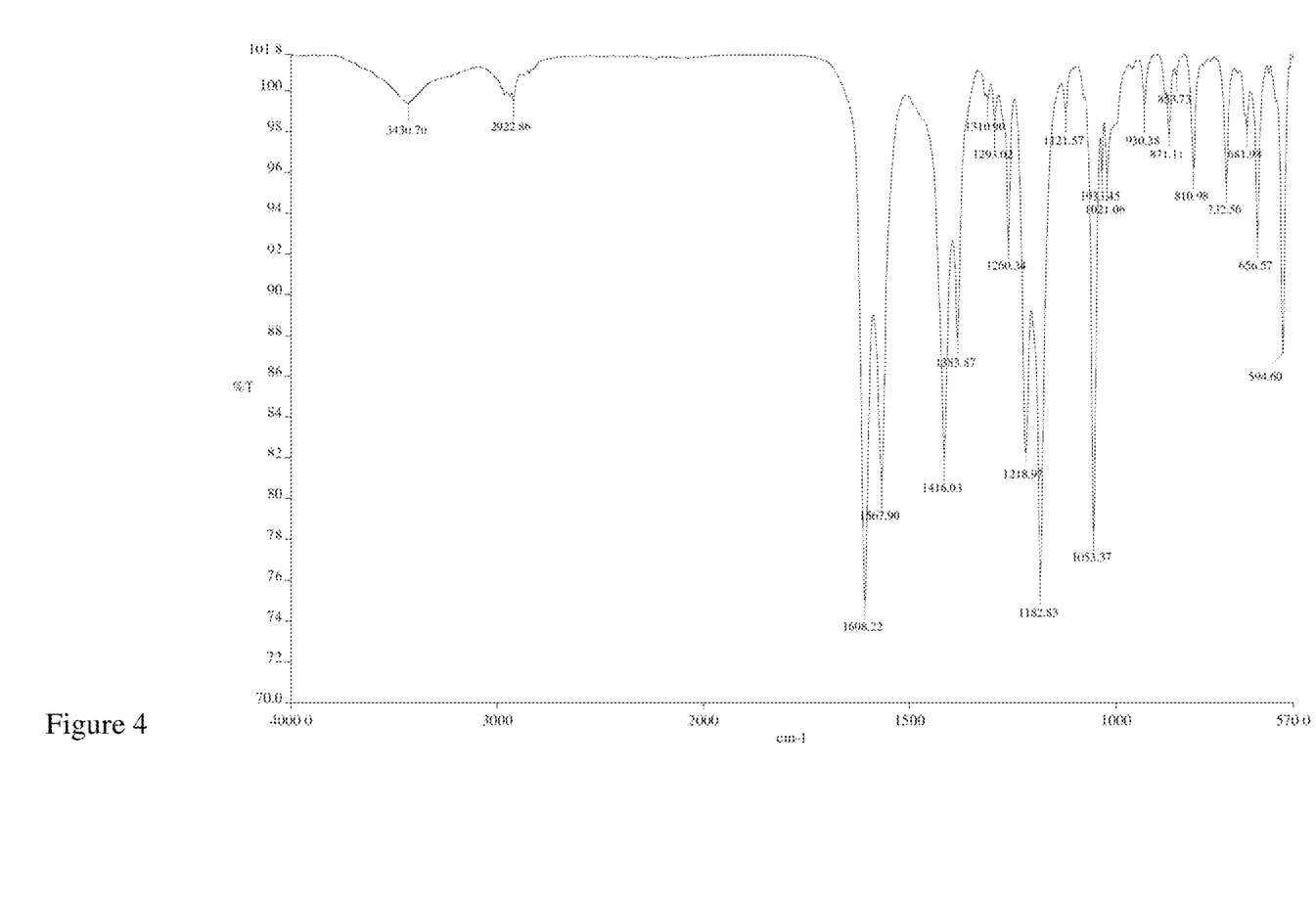
FIG. 4 shows the IR spectrum of the compound synthesized in Experiment 2 of the present invention.

The product of the aforesaid experiments was analyzed by NMR H1 spectrum and IR spectrum ($D_2O$ was used as solvent, conducted at room temperature). The results were shown in FIG. 3 and FIG. 4. According to the spectrum analysis, the compound synthesized in this experiment has the following structure:

(Sample 4)

Lastly, the Sample 4 compound was dissolved in water and formulated as electroplating additive of 0.05, 1, and 10 weight % respectively.

Experiment 3: Examination to the Effects of the Present Compound in Electroplating—I This experiment conducted electroplating by using the sample 1 compound synthesized in the experiment 1 above and examined its effects. The electroplating solution of this experiment comprised: 220 g/L of $CuSO_4.5H_2O$, 38.5 mL of $H_2SO_4$, 0.1 g/L of the compound synthesized in the experiment 1 above (ie. Sample 1, named MAPS)) or 3-mercapto-1-propanesulfonate (MPS, as control group), 0.16 g/L of NaCl, 0.06 g/L of PEG (MW=6000), and the water as the remaining part. This experiment used the Sample 1 compound of Experiment 1 for formulating the electroplating solution. Those having ordinary skill in the art can also use the electroplating additives made in Experiment 1 for formulating the electroplating solution as long as obtained electroplating solution contained 0.1 g/L of the sample 1 compound then it would be the electroplating solution required in this experiment.

Figure 5:
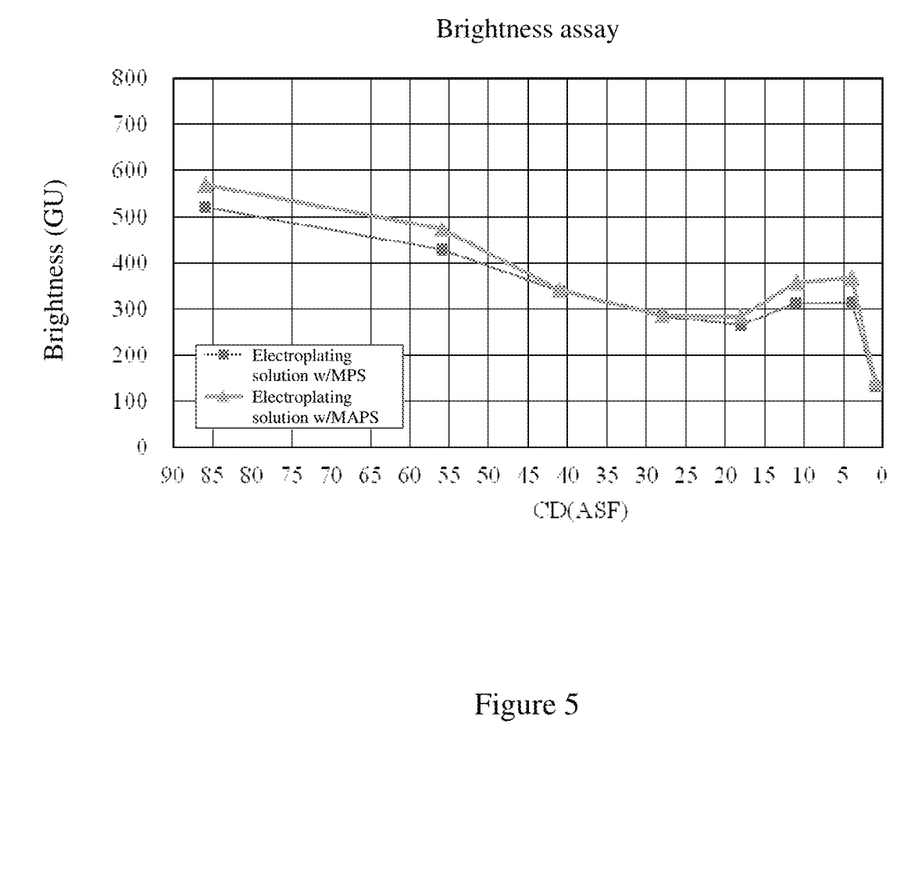
FIG. 5 exhibits the result of brightness test in the Experiment 3 of the present invention.

250 mL of the aforesaid electroplating solutions were respectively introduced into Hull cells. Brass strip pre-treated with 5 wt % of degreasing agent was used as cathode. The electroplating was conducted for 2 minutes at current 2 A and at room temperature. Afterward, the strips were washed by purified water and immersed in 5 wt % of sulfuric acid solution. Then, the strips were washed again by purified water and dried afterward. The brightness of those strips were measured by a brightness test meter and the results were shown in FIG. 5. It is noted that the strips electroplated by the electroplating solutions with the present electroplating additive (MAPS) in it have better brightness.

Figure 6:
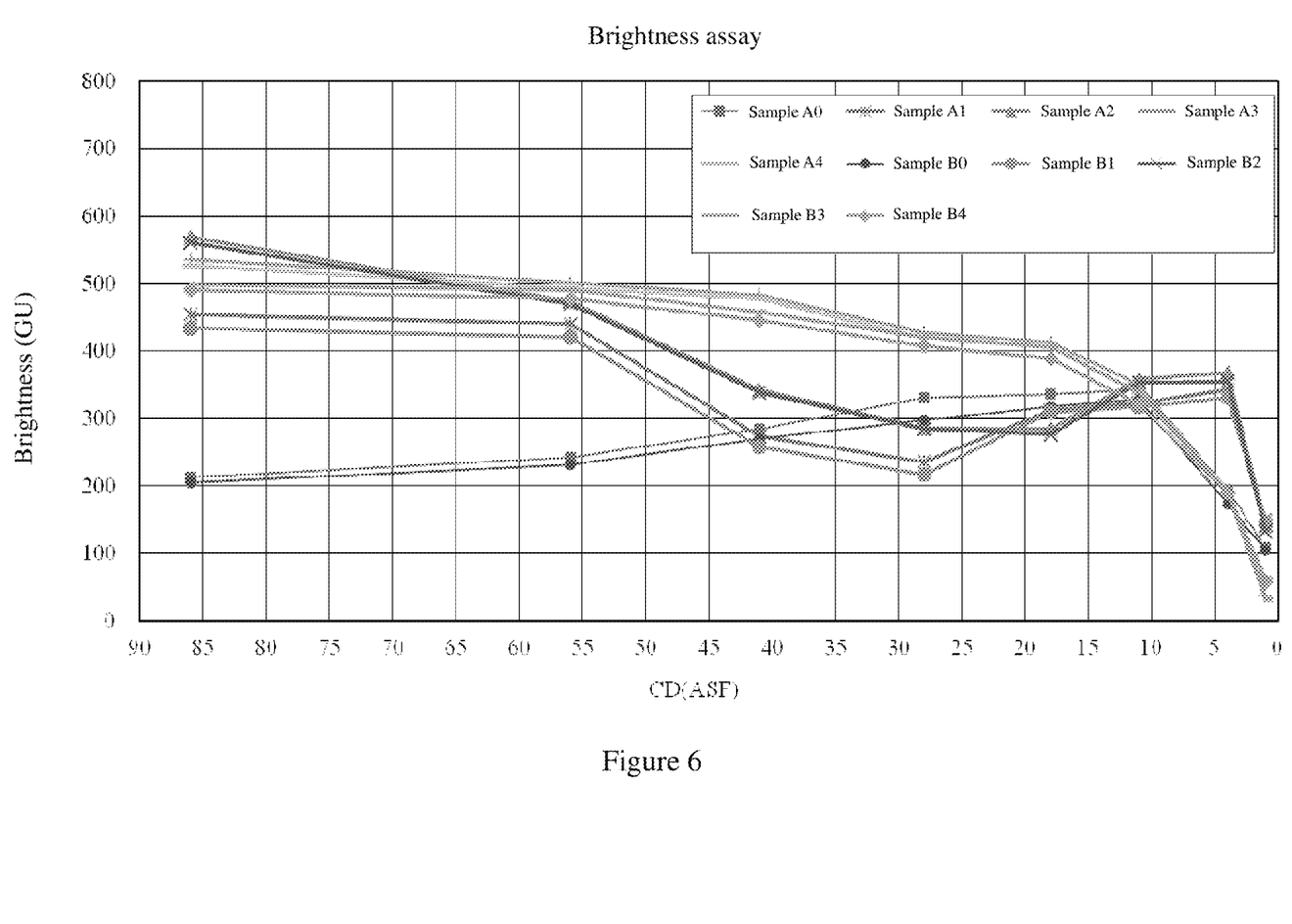
FIG. 6 exhibits the result of brightness test in the Experiment 4 of the present invention.

Experiment 4: Examination to the Effects of the Present Compound in Electroplating—II This experiment was conducted to test the electroplating effects of the electroplating solutions with various amount of the present compound added. The formulations of the electroplating solutions used in this experiment were listed in the following Table 3.250 mL of the aforesaid electroplating solutions were respectively introduced into Hull cells. Brass strip pre-treated with 5 wt % of degreasing agent was used as cathode. The electroplating was conducted for 2 minutes at currant 2 A and at room temperature. Afterward, the strips were washed by purified water and immersed in 5 wt % of sulfuric acid solution. Then, the strips were washed again by purified water and dried afterward. The strips were scanned for measuring cathodic cyclic voltammetry (CCV) thereof and the data were recorded in the following Table 4. The brightness of those strips was measured by a brightness test meter and the results were shown in the following Table 5 and FIG. 6.

This experiment used the Sample 1 compound synthesized in the Experiment 1 above for formulating the electroplating solution. Those having ordinary skill in the art can also use the electroplating additives prepared in Experiment 1 for formulating the electroplating solution as long as the obtained electroplating solution contained 0.1 g/L of the Sample 1 compound then it would be the electroplating solution required in this experiment.

TABLE 3

Formulation of the electroplating solutions for Experiment 4

| electroplating solution samples | CuSO₄•5H₂O | H₂SO₄ | NaCl | PEG6000 | MAPS |
|---|---|---|---|---|---|
| electroplating solution A0 | 220 g/L | 38.5 m/L | 0.16 g/L | None | None |
| electroplating solution A1 | 220 g/L | 38.5 m/L | 0.16 g/L | 0.06 g/L | 0.05 g/L |
| electroplating solution A2 | 220 g/L | 38.5 m/L | 0.16 g/L | 0.06 g/L | 0.1 g/L |
| electroplating solution A3 | 220 g/L | 38.5 m/L | 0.16 g/L | 0.06 g/L | 0.15 g/L |
| electroplating solution A4 | 220 g/L | 38.5 m/L | 0.16 g/L | 0.06 g/L | 0.2 g/L |
| electroplating solution B0 | 220 g/L | 60 m/L | None | None | None |
| electroplating solution B1 | 220 g/L | 60 m/L | None | 0.06 g/L | 0.05 g/L |
| electroplating solution B2 | 220 g/L | 60 m/L | None | 0.06 g/L | 0.1 g/L |
| electroplating solution B3 | 220 g/L | 60 m/L | None | 0.06 g/L | 0.15 g/L |
| electroplating solution B4 | 220 g/L | 60 m/L | None | 0.06 g/L | 0.2 g/L |

TABLE 4

Results of cathodic cyclic voltammetry scanning

| electroplating solution samples | Current (A) | CCV (V) |
|---|---|---|
| electroplating solution A0 | 2.00 | 2.41 |
| electroplating solution A1 | 2.00 | 2.29 |
| electroplating solution A2 | 2.00 | 2.12 |
| electroplating solution A3 | 2.00 | 2.40 |
| electroplating solution A4 | 2.00 | 2.53 |
| electroplating solution B0 | 2.00 | 2.40 |
| electroplating solution B1 | 2.00 | 2.31 |
| electroplating solution B2 | 2.00 | 2.15 |
| electroplating solution B3 | 2.00 | 2.41 |
| electroplating solution B4 | 2.00 | 2.55 |

TABLE 5

Results of brightness assay

| electroplating solution samples | Current Density (ASF) | | | | | | | |
|---|---|---|---|---|---|---|---|---|
| | 86 | 56 | 41 | 28 | 18 | 11 | 4 | 1 |
| electroplating solution A0 | 213.0 | 242.0 | 284.0 | 330.0 | 336.0 | 343.0 | 195.0 | 108.0 |
| electroplating solution A1 | 453.0 | 440.0 | 274.0 | 236.0 | 312.0 | 323.0 | 343.0 | 150.0 |
| electroplating solution A2 | 569.0 | 473.0 | 342.0 | 286.0 | 285.0 | 358.0 | 367.0 | 141.0 |
| electroplating solution A3 | 536.0 | 501.0 | 482.0 | 427.0 | 413.0 | 350.0 | 192.0 | 37.0 |
| electroplating solution A4 | 526.0 | 493.0 | 478.0 | 419.0 | 406.0 | 339.0 | 191.0 | 64.0 |
| electroplating solution B0 | 205.0 | 231.0 | 270.0 | 298.0 | 318.0 | 328.0 | 174.0 | 104.0 |
| electroplating solution B1 | 434.0 | 421.0 | 258.0 | 217.0 | 309.0 | 317.0 | 331.0 | 145.0 |
| electroplating solution B2 | 561.0 | 469.0 | 338.0 | 285.0 | 276.0 | 353.0 | 355.0 | 133.0 |
| electroplating solution B3 | 499.0 | 490.0 | 458.0 | 421.0 | 406.0 | 338.0 | 190.0 | 32.0 |
| electroplating solution B4 | 491.0 | 478.0 | 446.0 | 407.0 | 389.0 | 321.0 | 189.0 | 59.0 |

According to the data shown in Table 4, it confirmed the present MAPS compound would not negatively affect the electroplating procedures. Besides, from the data shown in Table 5 and FIG. 6, it was noted that the present MAPS compound was able to offer better brightness under both high current density and low current density.

The invention claimed is:

1. A carboxyl sulfonate compound of formula (A):

(A)

wherein,
$M_1$ is hydrogen or an alkali metal;
$M_2$ is hydrogen, alkyl, or an alkali metal;
each Y is independently hydrogen, alkyl, carboxyl, carboxyl salt, alkylcarboxyl, or alkylcarboxyl salt or ester;
n is an integer from 1 to 10; and
m is an integer from 1 to 10;
provided that at least one of Y is carboxyl, carboxyl salt, alkylcarboxyl, alkylcarboxyl salt or ester.

2. The carboxyl sulfonate compound of claim 1, wherein each Y is independently of formula (B):

(B)

wherein $M_3$ is hydrogen, alkyl, or alkali metal; and *C represent a bond connecting formula (B) to formula (A).

3. The carboxyl sulfonate compound of claim 1, wherein said alkali metal of $M_1$ and/or said alkali metal of $M_2$ are lithium, sodium, or potassium.

4. The carboxyl sulfonate compound of claim 1, wherein said alkyl of $M_2$ is $C_1$-$C_3$ alkyl.

5. The carboxyl sulfonate compound of claim 2, wherein at least one of $M_2$ and $M_3$ is an alkali metal.

6. The carboxyl sulfonate compound of claim 2, wherein $M_1$ is an alkali metal, $M_2$ and $M_3$ are both hydrogen, n is 3, and m is 1.

7. The carboxyl sulfonate compound of claim 2, wherein $M_1$ is an alkali metal, $M_2$ and $M_3$ are both alkyl, n is 3, and m is 1.

8. The carboxyl sulfonate compound of claim 2, wherein $M_1$ is an alkali metal, one of $M_2$ and $M_3$ is alkyl and the other one is an alkali metal, n is 3, and m is 1.

9. The carboxyl sulfonate compound of claim 1, wherein said compound is of formula (C):

(C)

wherein,
$M_1$ is hydrogen or an alkali metal;
$M_2$ is hydrogen, alkyl, or an alkali metal;
$Y_1$ and $Y_2$ are independently hydrogen, alkyl, carboxyl, carboxyl salt, alkylcarboxyl, or alkylcarboxyl salt; and
n is an integer from 1 to 10.

10. The carboxyl sulfonate compound of claim 9, wherein $M_1$ is an alkali metal, $M_2$ is hydrogen, n is 3, $Y_1$ is hydrogen, $Y_2$ is hydrogen or alkyl.

11. The carboxyl sulfonate compound of claim 2, wherein said alkali metal of $M_3$ is lithium, sodium, or potassium.

12. The carboxyl sulfonate compound of claim 2, wherein said alkyl of $M_3$ is $C_1$-$C_3$ alkyl.

13. An electroplating additive, comprising:
the carboxyl sulfonate compound of claim 1; and
a solvent;
wherein a weight percent of said carboxyl sulfonate compound is 0.01 to 50 weight percent of said electroplating additive based on a total weight thereof at a temperature of 27±3° C.

14. The electroplating additive of claim 13, wherein said solvent is water.

15. The electroplating additive of claim 13, wherein said electroplating is lead-free plating, copper plating, tin plating, nickel plating, or a combination thereof.

* * * * *